United States Patent [19]

Spreyer et al.

[11] Patent Number: 5,643,750
[45] Date of Patent: Jul. 1, 1997

[54] HUMAN NEURONAL BETA SUBUNITS OF VOLTAGE-OPERATED CALCIUM CHANNELS AND THE USE THEREOF

[75] Inventors: Peter Spreyer, Duesseldorf; Axel Unterbeck, Bergisch Gladbach, both of Germany

[73] Assignee: Bayer Aktiengesellschaft, Leverkusen, Germany

[21] Appl. No.: 343,733

[22] Filed: Nov. 21, 1994

Related U.S. Application Data

[63] Continuation of Ser. No. 15,495, Feb. 9, 1993, abandoned.

[30] Foreign Application Priority Data

Feb. 17, 1992 [DE] Germany .................. 42 04 716.1
Jul. 6, 1992 [DE] Germany .................. 42 22 126.9

[51] Int. Cl.$^6$ .................. C07K 14/47; C12N 15/12; C12P 21/00; C12Q 1/68
[52] U.S. Cl. .................. 435/69.1; 435/6; 435/172.3; 435/348; 435/325; 530/350; 536/23.5
[58] Field of Search .................. 536/23.5; 530/350; 435/70.1, 70.3, 69.1, 240.2, 6, 7.2

[56] References Cited

U.S. PATENT DOCUMENTS

| | | | |
|---|---|---|---|
| 4,950,739 | 8/1990 | Cherksey et al. | 530/350 |
| 5,386,025 | 1/1995 | Jay et al. | 536/23.5 |
| 5,429,921 | 7/1995 | Harpold et al. | 435/4 |

OTHER PUBLICATIONS

Williams, M.E. et al; Neuron 8;71–84 (Jan. 1992).
Varadi, G. et al.; Nature 352:159–162 (1991).
Catterall, W.A.; Science 253:1499–1500 (1991).
Miller, R.J.; J. Biol. Chem. 267:1403–1406 (Jan. 1992).
Catterall, Curr. Opin. Neurobiol. 1:5–13 (1991).
Tsien et al., 1988, Trends in Neurol. Sci., 11:431–439.
Tanabe et al., 1987, Nature 328:313–318.
Singer et al., 1991, Science 253:1553.
Lacerda et al., 1991, Nature 352:527.
Varadi et al., 1991, Nature 352:159.
Ruth et al., 1989, Science 245:1115.
Gluzman, 1981, Cell 23:175.
Chen et al., 1987, Mol. Cell. Biol. 7:2745–2752.
Messing et al., 1985, J. Pharmacology and Exp. Therapeutics 235:407–411.
Rosario et al., 1989, Neurosci. 29, 735–747.
Carbone et al., 1990, Pflugers Arch., 416:170–179.
Zernig et al., 1986, Eur. J. Pharmacol. 128, 221–229.
Yool and Schwarz, 1991, Nature, 349:700–704.

*Primary Examiner*—Robert A. Wax
*Assistant Examiner*—Eric Grimes
*Attorney, Agent, or Firm*—Sprung Horn Kramer & Woods

[57] ABSTRACT

The present invention relates to human neuronal beta subunits of voltage-operated calcium channels and the use thereof in screening methods for finding pharmaceuticals which modulate the activity of these calcium channels.

9 Claims, No Drawings

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 1612 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: NO ( i v ) ANTI-SENSE: NO ( v ) FRAGMENT TYPE: N-terminal ( v i ) ORIGINAL SOURCE:
        ( C ) INDIVIDUAL ISOLATE: Human
        ( F ) TISSUE TYPE: brain ( v i i ) IMMEDIATE SOURCE:
        ( B ) CLONE: Lamda ZAPII ( x i ) SEQUENCE DESCRIPTION: SEQ ID NO: 1:

```
GAGGGGAGGC  TCCTCTCC  ATG  GTC  CAG  AAG  ACC  AGC  ATG              39
                      Met  Val  Gln  Lys  Thr  Ser  Met
                       1                   5

TCC  CGG  GGC  CCT  TAC  CCA  CCC  TCC  CAG  GAG  ATC  CCC  ATG      78
Ser  Arg  Gly  Pro  Tyr  Pro  Pro  Ser  Gln  Glu  Ile  Pro  Met
          10                   15                             20

GAG  GTC  TTC  GAC  CCC  AGC  CCG  CAG  GGC  AAA  TAC  AGC  AAG      117
Glu  Val  Phe  Asp  Pro  Ser  Pro  Gln  Gly  Lys  Tyr  Ser  Lys
                    25                        30

AGG  AAA  GGG  CGA  TTC  AAA  CGG  TCA  GAT  GGG  AGC  ACG  TCC      156
Arg  Lys  Gly  Arg  Phe  Lys  Arg  Ser  Asp  Gly  Ser  Thr  Ser
          35                   40                        45

TCG  GAT  ACC  ACA  TCC  AAC  AGC  TTT  GTC  CGC  CAG  GGC  TCA      195
Ser  Asp  Thr  Thr  Ser  Asn  Ser  Phe  Val  Arg  Gln  Gly  Ser
               50                        55

GCG  GAG  TCC  TAC  ACC  AGC  CGA  CCA  TCA  GAC  TCT  GAT  GTA      234
Ala  Glu  Ser  Tyr  Thr  Ser  Arg  Pro  Ser  Asp  Ser  Asp  Val
 60                        65                        70

TCT  CTG  GAG  GAG  GAC  CGG  GAA  GCC  TTA  AGG  AAG  GAA  GCA      273
Ser  Leu  Glu  Glu  Asp  Arg  Glu  Ala  Leu  Arg  Lys  Glu  Ala
               75                        80                   85

GAG  CGC  CAG  GCA  TTA  GCG  CAG  CTC  GAG  AAG  GCC  AAG  ACC      312
Glu  Arg  Gln  Ala  Leu  Ala  Gln  Leu  Glu  Lys  Ala  Lys  Thr
                    90                        95

AAG  CCA  GTG  GCA  TTT  GCT  GTG  CGG  ACA  AAT  GTT  GGC  TAC      351
Lys  Pro  Val  Ala  Phe  Ala  Val  Arg  Thr  Asn  Val  Gly  Tyr
     100                        105                      110

AAT  CCG  TCT  CCA  GGG  GAT  GAG  GTG  CCT  GTG  CAG  GGA  GTG      390
Asn  Pro  Ser  Pro  Gly  Asp  Glu  Val  Pro  Val  Gln  Gly  Val
               115                       120

GCC  ATC  ACC  TTC  GAG  CCC  AAA  GAC  TTC  CTG  CAC  ATC  AAG      429
Ala  Ile  Thr  Phe  Glu  Pro  Lys  Asp  Phe  Leu  His  Ile  Lys
 125                       130                       135
```

-continued

| | | | | | | | | | | | | |
|---|---|---|---|---|---|---|---|---|---|---|---|---|
| GAG | AAA | TAC | AAT | AAT | GAC | TGG | TGG | ATC | GGG | CGG | CTG | GTG | 468 |
| Glu | Lys | Tyr | Asn | Asn | Asp | Trp | Trp | Ile | Gly | Arg | Leu | Val |
| | | 140 | | | | 145 | | | | | | 150 |
| AAG | GAG | GGC | TGT | GAG | GTT | GGC | TTC | ATT | CCC | AGC | CCC | GTC | 507 |
| Lys | Glu | Gly | Cys | Glu | Val | Gly | Phe | Ile | Pro | Ser | Pro | Val |
| | | | | 155 | | | | | 160 | | | |
| AAA | CTG | GAC | AGC | CTT | CGC | CTG | CTG | CAG | GAA | CAG | AAG | CTG | 546 |
| Lys | Leu | Asp | Ser | Leu | Arg | Leu | Leu | Gln | Glu | Gln | Lys | Leu |
| | 165 | | | | | 170 | | | | | 175 | |
| CGC | CAG | AAC | CGC | CTC | GGC | TCC | AGC | AAA | TCA | GGC | GAT | AAC | 585 |
| Arg | Gln | Asn | Arg | Leu | Gly | Ser | Ser | Lys | Ser | Gly | Asp | Asn |
| | | | 180 | | | | | 185 | | | | |
| TCC | AGT | TCC | AGT | CTG | GGA | GAT | GTG | GTG | ACT | GGC | ACC | CGC | 624 |
| Ser | Ser | Ser | Ser | Leu | Gly | Asp | Val | Val | Thr | Gly | Thr | Arg |
| 190 | | | | | 195 | | | | | 200 | | |
| CGC | CCC | ACA | CCC | CCT | GCC | AGT | GCC | AAA | CAG | AAG | CAG | AAG | 663 |
| Arg | Pro | Thr | Pro | Pro | Ala | Ser | Ala | Lys | Gln | Lys | Gln | Lys |
| | | 205 | | | | | 210 | | | | | 215 |
| TCG | ACA | GAG | CAT | GTG | CCC | CCC | TAT | GAC | GTG | GTG | CCT | TCC | 702 |
| Ser | Thr | Glu | His | Val | Pro | Pro | Tyr | Asp | Val | Val | Pro | Ser |
| | | | | 220 | | | | | 225 | | | |
| ATG | AGG | CCC | ATC | ATC | CTG | GTG | GGA | CCG | TCG | CTC | AAG | GGC | 741 |
| Met | Arg | Pro | Ile | Ile | Leu | Val | Gly | Pro | Ser | Leu | Lys | Gly |
| | 230 | | | | | 235 | | | | | 240 | |
| TAC | GAG | GTT | ACA | GAC | ATG | ATG | CAG | AAA | GCT | TTA | TTT | GAC | 780 |
| Tyr | Glu | Val | Thr | Asp | Met | Met | Gln | Lys | Ala | Leu | Phe | Asp |
| | | | 245 | | | | | 250 | | | | |
| TTC | TTG | AAG | CAT | CGG | TTT | GAT | GGC | AGG | ATC | TCC | ATC | ACT | 819 |
| Phe | Leu | Lys | His | Arg | Phe | Asp | Gly | Arg | Ile | Ser | Ile | Thr |
| 255 | | | | | 260 | | | | | 265 | | |
| CGT | GTG | ACG | GCA | GAT | ATT | TCC | CTG | GCT | AAG | CGC | TCA | GTT | 858 |
| Arg | Val | Thr | Ala | Asp | Ile | Ser | Leu | Ala | Lys | Arg | Ser | Val |
| | | 270 | | | | | 275 | | | | | 280 |
| CTC | AAC | AAC | CCC | AGC | AAA | CAC | ATC | ATC | ATT | GAG | CGC | TCC | 897 |
| Leu | Asn | Asn | Pro | Ser | Lys | His | Ile | Ile | Ile | Glu | Arg | Ser |
| | | | | 285 | | | | | 290 | | | |
| AAC | ACA | CGC | TCC | AGC | CTG | GCT | GAG | GTG | CAG | AGT | GAA | ATC | 936 |
| Asn | Thr | Arg | Ser | Ser | Leu | Ala | Glu | Val | Gln | Ser | Glu | Ile |
| | 295 | | | | | 300 | | | | | 305 | |
| GAG | CGA | ATC | TTC | GAG | CTG | GCC | CGG | ACC | CTT | CAG | TTG | GTC | 975 |
| Glu | Arg | Ile | Phe | Glu | Leu | Ala | Arg | Thr | Leu | Gln | Leu | Val |
| | | | 310 | | | | | 315 | | | | |
| GCT | CTG | GAT | GCT | GAC | ACC | ATC | AAT | CAC | CCA | GCC | CAG | CTG | 1014 |
| Ala | Leu | Asp | Ala | Asp | Thr | Ile | Asn | His | Pro | Ala | Gln | Leu |
| 320 | | | | | 325 | | | | | 330 | | |
| TCC | AAG | ACC | TCG | CTG | GCC | CCC | ATC | ATT | GTT | TAC | ATC | AAG | 1053 |
| Ser | Lys | Thr | Ser | Leu | Ala | Pro | Ile | Ile | Val | Tyr | Ile | Lys |
| | | 335 | | | | | 340 | | | | | 345 |
| ATC | ACC | TCT | CCC | AAG | GTA | CTT | CAA | AGG | CTC | ATC | AAG | TCC | 1092 |
| Ile | Thr | Ser | Pro | Lys | Val | Leu | Gln | Arg | Leu | Ile | Lys | Ser |
| | | | | 350 | | | | | 355 | | | |
| CGA | GGA | AAG | TCT | CAG | TCC | AAA | CAC | CTC | AAT | GTC | CAA | ATA | 1131 |
| Arg | Gly | Lys | Ser | Gln | Ser | Lys | His | Leu | Asn | Val | Gln | Ile |
| | 360 | | | | | 365 | | | | | 370 | |
| GCG | GCC | TCG | GAA | AAG | CTG | GCA | CAG | TGC | CCC | CCT | GAA | ATG | 1170 |
| Ala | Ala | Ser | Glu | Lys | Leu | Ala | Gln | Cys | Pro | Pro | Glu | Met |
| | | | 375 | | | | | 380 | | | | |
| TTT | GAC | ATC | ATC | CTG | GAT | GAG | AAC | CAA | TTG | GAG | GAT | GCC | 1209 |
| Phe | Asp | Ile | Ile | Leu | Asp | Glu | Asn | Gln | Leu | Glu | Asp | Ala |
| 385 | | | | | 390 | | | | | 395 | | |

| | |
|---|---|
| TGC GAG CAT CTG GCG GAG TAC TTG GAA GCC TAT TGG AAG<br>Cys Glu His Leu Ala Glu Tyr Leu Glu Ala Tyr Trp Lys<br>400              405              410 | 1248 |
| GCC ACA CAC CCG CCC AGC AGC ACG CCA CCC AAT CCG CTG<br>Ala Thr His Pro Pro Ser Ser Thr Pro Pro Asn Pro Leu<br>              415              420 | 1287 |
| CTG AAC CGC ACC ATG GCT ACC GCA GCC CTG GCT GCC AGC<br>Leu Asn Arg Thr Met Ala Thr Ala Ala Leu Ala Ala Ser<br>425              430              435 | 1326 |
| CCT GCC CCT GTC TCC AAC CTC CAG GTA CAG GTG CTC ACC<br>Pro Ala Pro Val Ser Asn Leu Gln Val Gln Val Leu Thr<br>              440              445 | 1365 |
| TCG CTC AGG AGA AAC CTC GGC TTC TGG GGC GGG CTG GAG<br>Ser Leu Arg Arg Asn Leu Gly Phe Trp Gly Gly Leu Glu<br>450              455              460 | 1404 |
| TCC TCA CAG CGG GGC AGT GTG GTG CCC CAG GAG CAG GAA<br>Ser Ser Gln Arg Gly Ser Val Val Pro Gln Glu Gln Glu<br>              465              470              475 | 1443 |
| CAT GCC ATG TAGTGGGCGC CCTGCCCGTC TTCCTCCTG<br>His Ala Met | 1482 |
| CTCTGGGGTC GGAACTGGAG TGCAGGGAAC ATGGAGGAGG | 1522 |
| AAGGGAAGAG CTTTATTTTG TAAAAAAATA AGATGAGCGG | 1562 |
| CAAGGAATTC GATATCAAGC TTATCGATAC CGTCGACCTC | 1602 |
| GAGGGGGGGC | 1612 |

( 2 ) INFORMATION FOR SEQ ID NO: 2:

( i ) SEQUENCE CHARACTERISTICS:
        ( A ) LENGTH: 1830 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: NO ( i v ) ANTI-SENSE: NO ( v ) FRAGMENT TYPE: N-terminal ( v i ) ORIGINAL SOURCE:
        ( C ) INDIVIDUAL ISOLATE: Human
        ( F ) TISSUE TYPE: Brain ( v i i ) IMMEDIATE SOURCE:
        ( B ) CLONE: Lamda ZAPII ( x i ) SEQUENCE DESCRIPTION: SEQ ID NO: 2:

| | |
|---|---|
| CCCAAGCTCG AAATTAACCC TCACTAAAGG GAACAAAAGC | 40 |
| TGGAGCTCCA CCGCGGTGGC GGCCGCTCTA GAACTAGTGG | 80 |
| ATCCCCCGGG CTGCAGGAAT TCCCGGACTC CCCC ATG TAT<br>                                                            Met Tyr<br>                                                             1 | 120 |
| GAC GAC TCC TAC GTG CCC GGG TTT GAG GAC TCG GAG GCG<br>Asp Asp Ser Tyr Val Pro Gly Phe Glu Asp Ser Glu Ala<br>            5                      10                      15 | 159 |
| GGT TCA GCC GAC TCC TAC ACC AGC CGC CCA TCT CTG GAC<br>Gly Ser Ala Asp Ser Tyr Thr Ser Arg Pro Ser Leu Asp<br>                   20                                25 | 198 |
| TCA GAC GTC TCC CTG GAG GAG GAC CGG GAG AGT GCC CGG<br>Ser Asp Val Ser Leu Glu Glu Asp Arg Glu Ser Ala Arg<br>30                              35                            40 | 237 |

```
CGT GAA GTA GAG AGC CAG GCT CAG CAG CAG CTC GAA AGG                276
Arg Glu Val Glu Ser Gln Ala Gln Gln Gln Leu Glu Arg
             45                  50

GCC AAG CAC AAA CCT GTG GCA TTT GCG GTG AGG ACC AAT                315
Ala Lys His Lys Pro Val Ala Phe Ala Val Arg Thr Asn
55                       60                  65

GTC AGC TAC TGT GGC GTA CTG GAT GAG GAG TGC CCA GTC                354
Val Ser Tyr Cys Gly Val Leu Asp Glu Glu Cys Pro Val
             70                  75                  80

CAG GGC TCT GGA GTC AAC TTT GAG GCC AAA GAT TTT CTG                393
Gln Gly Ser Gly Val Asn Phe Glu Ala Lys Asp Phe Leu
                 85                  90

CAC ATT AAA GAG AAG TAC AGC AAT GAC TGG TGG ATC GGG                432
His Ile Lys Glu Lys Tyr Ser Asn Asp Trp Trp Ile Gly
         95                 100                 105

CGG CTA GTG AAA GAG GGC GGG GAC ATC GCC TTC ATC CCC                471
Arg Leu Val Lys Glu Gly Gly Asp Ile Ala Phe Ile Pro
                110                 115

AGC CCC CAG CGC CTG GAG AGC ATC CGG CTC AAA CAG GAG                510
Ser Pro Gln Arg Leu Glu Ser Ile Arg Leu Lys Gln Glu
120                 125                 130

CAG AAG GCC AGG AGA TCT GGG AAC CCT TCC AGC CTG AGT                549
Gln Lys Ala Arg Arg Ser Gly Asn Pro Ser Ser Leu Ser
        135                 140                 145

GAC ATT GGC AAC CGA CGC TCC CCT CCG CCA TCT CTA GCC                588
Asp Ile Gly Asn Arg Arg Ser Pro Pro Pro Ser Leu Ala
                150                 155

AAG CAG AAG CAA AAG CAG GCG GAA CAT GTT CCC CCG TAT                627
Lys Gln Lys Gln Lys Gln Ala Glu His Val Pro Pro Tyr
160                 165                 170

GAC GTG GTG CCC TCC ATG CGG CCT GTG GTG CTG GTG GGA                666
Asp Val Val Pro Ser Met Arg Pro Val Val Leu Val Gly
                175                 180

CCC TCT CTG AAA GGT TAT GAG GTC ACA GAC ATG ATG CAG                705
Pro Ser Leu Lys Gly Tyr Glu Val Thr Asp Met Met Gln
185                 190                 195

AAG GCT CTC TTC GAC TTC CTC AAA CAC AGA TTT GAT GGC                744
Lys Ala Leu Phe Asp Phe Leu Lys His Arg Phe Asp Gly
        200                 205                 210

AGG ATC TCC ATC ACC CGA GTC ACA GCC GAC CTC TCC CTG                783
Arg Ile Ser Ile Thr Arg Val Thr Ala Asp Leu Ser Leu
                215                 220

GCA AAG CGA TCT GTG CTC AAC AAT CCG GGC AAG AGG ACC                822
Ala Lys Arg Ser Val Leu Asn Asn Pro Gly Lys Arg Thr
225                 230                 235

ATC ATT GAG CGC TCC TCT GCC CGC TCC AGC ATT GCG GAA                861
Ile Ile Glu Arg Ser Ser Ala Arg Ser Ser Ile Ala Glu
        240                 245

GTG CAG AGT GAG ATC GAG CGC ATA TTT GAG CTG GCC AAA                900
Val Gln Ser Glu Ile Glu Arg Ile Phe Glu Leu Ala Lys
250                 255                 260

TCC CTG CAG CTA GTA GTG TTG GAC GCT GAC ACC ATC AAC                939
Ser Leu Gln Leu Val Val Leu Asp Ala Asp Thr Ile Asn
        265                 270                 275

CAC CCA GCA CAG CTG GCC AAG ACC TCG CTG GCC CCC ATC                978
His Pro Ala Gln Leu Ala Lys Thr Ser Leu Ala Pro Ile
                280                 285

ATC GTC TTT GTC AAA GTG TCC TCA CCA AAG GTA CTC CAG               1017
Ile Val Phe Val Lys Val Ser Ser Pro Lys Val Leu Gln
290                 295                 300
```

```
CGT CTC ATT CGC TCC CGG GGG AAG TCA CAG ATG AAG CAC      1056
Arg Leu Ile Arg Ser Arg Gly Lys Ser Gln Met Lys His
        305                 310

CTG ACC GTA CAG ATG ATG GCA TAT GAT AAG CTG GTT CAG      1095
Leu Thr Val Gln Met Met Ala Tyr Asp Lys Leu Val Gln
315                     320                 325

TGC CCA CCG GAG TCA TTT GAT GTG ATT CTG GAT GAG AAC      1134
Cys Pro Pro Glu Ser Phe Asp Val Ile Leu Asp Glu Asn
            330             335                 340

CAG CTG GAG GAT GCC TGT GAG CAC CTG GCT GAG TAC CTG      1173
Gln Leu Glu Asp Ala Cys Glu His Leu Ala Glu Tyr Leu
                345                 350

GAG GTT TAC TGG CGG GCC ACG CAC CAC CCA GCC CCT GGC      1212
Glu Val Tyr Trp Arg Ala Thr His His Pro Ala Pro Gly
        355                 360                 365

CCC GGA CTT CTG GGT CCT CCC AGT GCC ATC CCC GGA CTT      1251
Pro Gly Leu Leu Gly Pro Pro Ser Ala Ile Pro Gly Leu
            370                 375

CAG AAC CAG CAG CTG CTG GGG GAG CGT GGC GAG GAG CAC      1290
Gln Asn Gln Gln Leu Leu Gly Glu Arg Gly Glu Glu His
380                     385                 390

TCC CCC CTT GAG CGG GAC AGC TTG ATG CCC TCT GAT GAG      1329
Ser Pro Leu Glu Arg Asp Ser Leu Met Pro Ser Asp Glu
            395                 400                 405

GCC AGC GAG ACG TCC CGC CAA GCC TGG ACA GGA TCT TCA      1368
Ala Ser Glu Thr Ser Arg Gln Ala Trp Thr Gly Ser Ser
                410                 415

CAG CGT ACG TCC CGC CAC CTG GAG GAG GAC TAT GCA GAT      1407
Gln Arg Thr Ser Arg His Leu Glu Glu Asp Tyr Ala Asp
        420                 425                 430

GCC TAC CAG GAC CTG TAC CAG CCT CAC CGC CAA CAC ACC      1446
Ala Tyr Gln Asp Leu Tyr Gln Pro His Arg Gln His Thr
            435                 440

TCG GGG CTG CCT AGT GCT AAC GGG CAT GAC CCC CAA GAC      1485
Ser Gly Leu Pro Ser Ala Asn Gly His Asp Pro Gln Asp
445                     450                 455

CGG CTT CTA GCC CAG GAC TCA GAA CAC AAC CAC AGT GAC      1524
Arg Leu Leu Ala Gln Asp Ser Glu His Asn His Ser Asp
            460                 465                 470

CGG AAC TGG CAG CGC AAC CGG CCT TGG CCC AAG GAT AGC      1563
Arg Asn Trp Gln Arg Asn Arg Pro Trp Pro Lys Asp Ser
                475                 480

TAC TGACAGCCTC CTGCTGCCCT ACCCTGGCAG GCACAGGCGC           1606
Tyr

AGCTGGCTGG GGGGCCCACT CCAGGCAGGG TGGCGTTAGA               1646

CTGGCATCAG GCTGGCACTA GGCTCAGCCC CCAAAACCCC               1686

CTGCCCAGCC CCAGCTTCAG GGCTGCCTGT GGTCCCAAGG               1726

TTCTGGGAGA AACAGGGGAC CCCCTCACCT CCTGGGCAGT               1766

GACCCCTACT AGGCTCCCAT TCCAGGTACT AGCTGTGTGT               1806

TCTGCACCCC TGGCACCGGA ATTC                                1830
```

( 2 ) INFORMATION FOR SEQ ID NO: 3:

( i ) SEQUENCE CHARACTERISTICS:
        ( A ) LENGTH: 1805 base pairs
        ( B ) TYPE: nucleic acid
        ( C ) STRANDEDNESS: single
        ( D ) TOPOLOGY: linear 5,643,750

15

16

-continued ( i i ) MOLECULE TYPE: genomic DNA ( i i i ) HYPOTHETICAL: NO ( i v ) ANTI-SENSE: NO ( v ) FRAGMENT TYPE: N-terminal ( v i ) ORIGINAL SOURCE:
    ( C ) INDIVIDUAL ISOLATE: Human
    ( F ) TISSUE TYPE: Brain ( v i i ) IMMEDIATE SOURCE:
    ( B ) CLONE: Lamda ZAPII ( x i ) SEQUENCE DESCRIPTION: SEQ ID NO: 3:

```
CCGCCGGGCC GGCGGCGGGA GGGGAGGCTC CTCTCC ATG GTC CAG              45
                                        Met Val Gln
                                          1

AAG ACC AGC ATG TCC CGG GGC CCT TAC CCA CCC TCC CAG              84
Lys Thr Ser Met Ser Arg Gly Pro Tyr Pro Pro Ser Gln
        5                  10                  15

GAG ATC CCC ATG GAG GTC TTC GAC CCC AGC CCG CAG GGC             123
Glu Ile Pro Met Glu Val Phe Asp Pro Ser Pro Gln Gly
                20                  25

AAA TAC AGC AAG AGG AAA GGG CGA TTC AAA CGG TCA GAT             162
Lys Tyr Ser Lys Arg Lys Gly Arg Phe Lys Arg Ser Asp
 30                  35                  40

GGG AGC ACG TCC TCG GAT ACC ACA TCC AAC AGC TTT GTC             201
Gly Ser Thr Ser Ser Asp Thr Thr Ser Asn Ser Phe Val
            45                  50                  55

CGC CAG GGC TCA GCG GAG TCC TAC ACC AGC CGA CCA TCA             240
Arg Gln Gly Ser Ala Glu Ser Tyr Thr Ser Arg Pro Ser
                60                  65

GAC TCT GAT GTA TCT CTG GAG GAG GAC CGG GAA GCC TTA             279
Asp Ser Asp Val Ser Leu Glu Glu Asp Arg Glu Ala Leu
         70                  75                  80

AGG AAG GAA GCA GAG CGC CAG GCA TTA GCG CAG CTC GAG             318
Arg Lys Glu Ala Glu Arg Gln Ala Leu Ala Gln Leu Glu
                 85                  90

AAG GCC AAG ACC AAG CCA GTG GCA TTT GCT GTG CGG ACA             357
Lys Ala Lys Thr Lys Pro Val Ala Phe Ala Val Arg Thr
 95                 100                 105

AAT GTT GGC TAC AAT CCG TCT CCA GGG GAT GAG GTG CCT             396
Asn Val Gly Tyr Asn Pro Ser Pro Gly Asp Glu Val Pro
             110                 115                 120

GTG CAG GGA GTG GCC ATC ACC TTC GAG CCC AAA GAC TTC             435
Val Gln Gly Val Ala Ile Thr Phe Glu Pro Lys Asp Phe
                 125                 130

CTG CAC ATC AAG GAG AAA TAC AAT AAT GAC TGG TGG ATC             474
Leu His Ile Lys Glu Lys Tyr Asn Asn Asp Trp Trp Ile
 135                 140                 145

GGG CGG CTG GTG AAG GAG GGC TGT GAG GTT GGC TTC ATT             513
Gly Arg Leu Val Lys Glu Gly Cys Glu Val Gly Phe Ile
             150                 155

CCC AGC CCC GTC AAA CTG GAC AGC CTT CGC CTG CTG CAG             552
Pro Ser Pro Val Lys Leu Asp Ser Leu Arg Leu Leu Gln
160                 165                 170

GAA CAG AAG CTG CGC CAG AAC CGC CTC GGC TCC AGC AAA             591
Glu Gln Lys Leu Arg Gln Asn Arg Leu Gly Ser Ser Lys
                 175                 180                 185

TCA GGC GAT AAC TCC AGT TCC AGT CTG GGA GAT GTG GTG             630
Ser Gly Asp Asn Ser Ser Ser Ser Leu Gly Asp Val Val
```

|     |     |     |     |     |     |     |     |     |     |     |     |     |
|-----|-----|-----|-----|-----|-----|-----|-----|-----|-----|-----|-----|-----|
|     |     |     |     | 190 |     |     |     |     | 195 |     |     |     |
| ACT | GGC | ACC | CGC | CGC | CCC | ACA | CCC | CCT | GCC | AGT | GCC | AAA | 669 |
| Thr | Gly | Thr | Arg | Arg | Pro | Thr | Pro | Pro | Ala | Ser | Ala | Lys |
|     | 200 |     |     |     |     | 205 |     |     |     |     | 210 |     |
| CAG | AAG | CAG | AAG | TCG | GTT | ACA | GAC | ATG | ATG | CAG | AAA | GCT | 708 |
| Gln | Lys | Gln | Lys | Ser | Val | Thr | Asp | Met | Met | Gln | Lys | Ala |
|     |     |     |     | 215 |     |     |     |     | 220 |     |     |     |
| TTA | TTT | GAC | TTC | TTG | AAG | CAT | CGG | TTT | GAT | GGC | AGG | ATC | 747 |
| Leu | Phe | Asp | Phe | Leu | Lys | His | Arg | Phe | Asp | Gly | Arg | Ile |
| 225 |     |     |     |     | 230 |     |     |     |     | 235 |     |     |
| TCC | ATC | ACT | CGT | GTG | ACG | GCA | GAT | ATT | TCC | CTG | GCT | AAG | 786 |
| Ser | Ile | Thr | Arg | Val | Thr | Ala | Asp | Ile | Ser | Leu | Ala | Lys |
|     |     |     | 240 |     |     |     |     | 245 |     |     |     | 250 |
| CGC | TCA | GTT | CTC | AAC | AAC | CCC | AGC | AAA | CAC | ATC | ATC | ATT | 825 |
| Arg | Ser | Val | Leu | Asn | Asn | Pro | Ser | Lys | His | Ile | Ile | Ile |
|     |     |     |     | 255 |     |     |     |     | 260 |     |     |     |
| GAG | CGC | TCC | AAC | ACA | CGC | TCC | AGC | CTG | GCT | GAG | GTG | CAG | 864 |
| Glu | Arg | Ser | Asn | Thr | Arg | Ser | Ser | Leu | Ala | Glu | Val | Gln |
|     | 265 |     |     |     |     | 270 |     |     |     |     | 275 |     |
| AGT | GAA | ATC | GAG | CGA | ATC | TTC | GAG | CTG | GCC | CGG | ACC | CTT | 903 |
| Ser | Glu | Ile | Glu | Arg | Ile | Phe | Glu | Leu | Ala | Arg | Thr | Leu |
|     |     |     | 280 |     |     |     |     | 285 |     |     |     |     |
| CAG | TTG | GTC | GCT | CTG | GAT | GCT | GAC | ACC | ATC | AAT | CAC | CCA | 942 |
| Gln | Leu | Val | Ala | Leu | Asp | Ala | Asp | Thr | Ile | Asn | His | Pro |
| 290 |     |     |     |     | 295 |     |     |     |     | 300 |     |     |
| GCC | CAG | CTG | TCC | AAG | ACC | TCG | CTG | GCC | CCC | ATC | ATT | GTT | 981 |
| Ala | Gln | Leu | Ser | Lys | Thr | Ser | Leu | Ala | Pro | Ile | Ile | Val |
|     |     | 305 |     |     |     |     | 310 |     |     |     |     | 315 |
| TAC | ATC | AAG | ATC | ACC | TCT | CCC | AAG | GTA | CTT | CAA | AGG | CTC | 1020 |
| Tyr | Ile | Lys | Ile | Thr | Ser | Pro | Lys | Val | Leu | Gln | Arg | Leu |
|     |     |     |     | 320 |     |     |     |     | 325 |     |     |     |
| ATC | AAG | TCC | CGA | GGA | AAG | TCT | CAG | TCC | AAA | CAC | CTC | AAT | 1059 |
| Ile | Lys | Ser | Arg | Gly | Lys | Ser | Gln | Ser | Lys | His | Leu | Asn |
|     | 330 |     |     |     |     | 335 |     |     |     |     | 340 |     |
| GTC | CAA | ATA | GCG | GCC | TCG | GAA | AAG | CTG | GCA | CAG | TGC | CCC | 1098 |
| Val | Gln | Ile | Ala | Ala | Ser | Glu | Lys | Leu | Ala | Gln | Cys | Pro |
|     |     |     | 345 |     |     |     |     | 350 |     |     |     |     |
| CCT | GAA | ATG | TTT | GAC | ATC | ATC | CTG | GAT | GAG | AAC | CAA | TTG | 1137 |
| Pro | Glu | Met | Phe | Asp | Ile | Ile | Leu | Asp | Glu | Asn | Gln | Leu |
| 355 |     |     |     |     | 360 |     |     |     |     | 365 |     |     |
| GAG | GAT | GCC | TGC | GAG | CAT | CTG | GCG | GAG | TAC | TTG | GAA | GCC | 1176 |
| Glu | Asp | Ala | Cys | Glu | His | Leu | Ala | Glu | Tyr | Leu | Glu | Ala |
|     |     | 370 |     |     |     |     | 375 |     |     |     |     | 380 |
| TAT | TGG | AAG | GCC | ACA | CAC | CCG | CCC | AGC | AGC | ACG | CCA | CCC | 1215 |
| Tyr | Trp | Lys | Ala | Thr | His | Pro | Pro | Ser | Ser | Thr | Pro | Pro |
|     |     |     |     | 385 |     |     |     |     | 390 |     |     |     |
| AAT | CCG | CTG | CTG | AAC | CGC | ACC | ATG | GCT | ACC | GCA | GCC | CTG | 1254 |
| Asn | Pro | Leu | Leu | Asn | Arg | Thr | Met | Ala | Thr | Ala | Ala | Leu |
|     | 395 |     |     |     |     | 400 |     |     |     |     | 405 |     |
| GCT | GCC | AGC | CCT | GCC | CCT | GTC | TCC | AAC | CTC | CAG | GGA | CCC | 1293 |
| Ala | Ala | Ser | Pro | Ala | Pro | Val | Ser | Asn | Leu | Gln | Gly | Pro |
|     |     |     | 410 |     |     |     |     | 415 |     |     |     |     |
| TAC | CTT | GCT | TCC | GGG | GAC | CAG | CCA | CTG | GAA | CGG | GCC | ACC | 1332 |
| Tyr | Leu | Ala | Ser | Gly | Asp | Gln | Pro | Leu | Glu | Arg | Ala | Thr |
| 420 |     |     |     |     | 425 |     |     |     |     | 430 |     |     |
| GGG | GAG | CAC | GCC | AGC | ATG | CAC | GAG | TAC | CCA | GGG | GAG | CTG | 1371 |
| Gly | Glu | His | Ala | Ser | Met | His | Glu | Tyr | Pro | Gly | Glu | Leu |
|     |     | 435 |     |     |     |     | 440 |     |     |     |     | 445 |
| GGC | CAG | CCC | CCA | GGC | CTT | TAC | CCC | AGC | AGC | CAC | CCA | CCA | 1410 |
| Gly | Gln | Pro | Pro | Gly | Leu | Tyr | Pro | Ser | Ser | His | Pro | Pro |

|     |     |     |     | 450 |     |     |     |     |     | 455 |     |      |
| --- | --- | --- | --- | --- | --- | --- | --- | --- | --- | --- | --- | ---- |
| GGC | CGG | GCA | GGC | ACG | CTA | CGG | GCA | CTG | TCC | CGC | CAA | GAC  | 1449
| Gly | Arg | Ala | Gly | Thr | Leu | Arg | Ala | Leu | Ser | Arg | Gln | Asp  |
|     | 460 |     |     |     |     | 465 |     |     |     |     | 470 |      |
| ACT | TTT | GAT | GCC | GAC | ACC | CCC | GGC | AGC | CGA | AAC | TCT | GCC  | 1488
| Thr | Phe | Asp | Ala | Asp | Thr | Pro | Gly | Ser | Arg | Asn | Ser | Ala  |
|     |     |     | 475 |     |     |     |     | 480 |     |     |     |      |
| TAC | ACG | GAG | CTG | GGA | GAC | TCA | TGT | GTG | GAC | ATG | GAG | ACT  | 1527
| Tyr | Thr | Glu | Leu | Gly | Asp | Ser | Cys | Val | Asp | Met | Glu | Thr  |
| 485 |     |     |     |     | 490 |     |     |     |     | 495 |     |      |
| GAC | CCC | TCA | GAG | GGG | CCA | GGG | CTT | GGA | GAC | CCT | GCA | GGG  | 1566
| Asp | Pro | Ser | Glu | Gly | Pro | Gly | Leu | Gly | Asp | Pro | Ala | Gly  |
|     |     | 500 |     |     |     |     | 505 |     |     |     |     | 510  |
| GGC | GGC | ACG | CCC | CCA | GCC | CGA | CAG | GGA | TCC | TGG | GAG | GAC  | 1605
| Gly | Gly | Thr | Pro | Pro | Ala | Arg | Gln | Gly | Ser | Trp | Glu | Asp  |
|     |     |     |     | 515 |     |     |     |     | 520 |     |     |      |
| GAG | GAA | GAA | GAC | TAT | GAG | GAA | GAG | CTG | ACC | GAC | AAC | CGG  | 1644
| Glu | Glu | Glu | Asp | Tyr | Glu | Glu | Glu | Leu | Thr | Asp | Asn | Arg  |
|     | 525 |     |     |     |     | 530 |     |     |     |     | 535 |      |
| AAC | CGG | GGC | CGG | AAT | AAG | GCC | CGC | TAC | TGC | GCT | GAG | GGT  | 1683
| Asn | Arg | Gly | Arg | Asn | Lys | Ala | Arg | Tyr | Cys | Ala | Glu | Gly  |
|     |     |     | 540 |     |     |     |     | 545 |     |     |     |      |
| GGG | GGT | CCA | GTT | TTG | GGG | CGC | AAC | AAG | AAT | GAG | CTG | GAG  | 1722
| Gly | Gly | Pro | Val | Leu | Gly | Arg | Asn | Lys | Asn | Glu | Leu | Glu  |
| 550 |     |     |     |     | 555 |     |     |     |     | 560 |     |      |
| GGC | TGG | GGA | CGA | GGC | GTC | TAC | ATT | CGC | TGAGAGGCAG |     |     |      | 1759
| Gly | Trp | Gly | Arg | Gly | Val | Tyr | Ile | Arg |     |     |     |      |
|     |     | 565 |     |     |     |     | 570 |     |     |     |     |      |

GGGCACACGG CGGGAGGAAG GGCTCTGAGC CAGGGGAGGG  1799

GAGGGA  1805

( 2 ) INFORMATION FOR SEQ ID NO: 4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

CTTAAGGCTT CCCGGTCCTC CTCCAGGGAG ACATCAGAGT  40

HUMAN NEURONAL BETA SUBUNITS OF VOLTAGE-OPERATED CALCIUM CHANNELS AND THE USE THEREOF

This application is a continuation of application Ser. No. 08/015,495 filed Feb. 9, 1993, now abandoned.

The present invention relates to human neuronal beta subunits of voltage-operated calcium channels and the use thereof in screening methods for finding pharmaceuticals.

Calcium ions have a wide variety of functions in every biological system. Cellular calcium homeostasis plays an essential part specifically in the physiology of nerve cells. The intracellular calcium concentration is about 0.1 μM, compared with 1 mM outside the nerve cell. This steep concentration gradient (×10,000) is regulated primarily by voltage-operated calcium channels (VOCC) which can be blocked by certain calcium antagonists. During a cerebral ischaemia (stroke) there is a considerable change in the calcium homeostasis in neurons in the area affected by the infarct. The voltage-operated calcium channels are kept in the open state by prolonged membrane depolarisations, the consequence of which is a massive influx of calcium ions. The intracellular calcium concentration increases 1000-fold during this. The large excess of calcium activates, owing to the binding to calmodulin, various calcium/calmodulin-dependent cellular enzyme systems, such as kinases, proteases and phospholipases, which together lead, when activation is prolonged, to irreversible damage to nerve cells.

One therapeutic approach to neuroprotection in cerebral ischemia is reversible blockade of the massive influx of calcium into the nerve cell. The voltage-operated neuronal calcium channels are a suitable pharmacological target in this case. The VOCCs exist in various muscle cells (vascular, cardiac and skeletal muscle), neurons and secretory cells with tissue-specific physio-logical properties.

Electrophysiological investigations (Tsien et al., 1988, Trends in Neurol. Sci 11: 431–438) indicate that there are at least three different types of VOCCs (L, N and T channels). The 1,4-dihydropyridines (DHPs) are potent blockers of L type calcium channels which are found both in muscle cells and in nerve cells. The rabbit skeletal muscle dihydropyridine receptor has been biochemically characterised and cloned (Tanabe et al., 1987, Nature 328: 313–318). The primary sequence of this α1 SU of the VOCC has been derived from the cDNA data and is consistent with a 212 kD transmembrane protein with five N-glycosylation sites and seven possible phosphorylation sites. The protein contains four mutually similar trans-membrane domains, each of which has six—presumably α-helical—transmembrane segments (S1-S6). The fourth transmembrane segment (S4) of each domain contains an ordered pattern of positive charges (Lys, Arg) which may form the voltage sensor of the calcium channel. The structure of this cloned α1 SU is consistent with an ion-conducting, voltage-controlled unit of the DHP-sensitive calcium channel.

Besides the alpha-1 subunit, which forms the actual calcium channel, four other proteins are involved in the structure of the complete channel complex, which are called the alpha-2, beta, gamma and delta subunits.

Recent investigations have shown, that, in particular, the beta subunit influences important parameters of channel function: when the $\alpha_1$ and $\beta$ SUs are expressed together in vitro there is a change in the calcium flux, the activation and inactivation kinetics of the channel complex, and the binding affinity for dihydropyridines (Singer et al., 1991, Science 253: 1553; Lacerda et al., 1991, Nature 352: 527; Varadi et al., 1991, Nature 352: 159).

Thus, the availability of complete cDNA clones of the beta subunit is of great importance for the reconstitution of a physiologically relevant channel structure by gene expression in eukaryotic cells.

It was possible with the aid of an oligonucleotide which was derived from the DNA sequence of the beta subunit from rabbit skeletal muscle (Ruth et al., 1989, Science 245: 1115) to isolate 3 different cDNA types which encode human neuronal beta subunits. The cloned beta subunits are to be expressed together with subtypes, which are already present, of neuronal alpha-1 clones in transformed animal cells (for example cos cells, mouse L cells, CHO cells etc) (Gluzman, 1981, Cell 23: 175 and Chen et al., 1987, Mol. Cell. Biol. 7: 2745-2752). These constructs are employed in binding assays and/or functional assay systems which are used to find novel subtype-specific ligands of neuronal calcium channels.

These recombinant cell systems are furthermore to be used to develop functional calcium flux assays with the aid of which it is possible to check the agonistic or antagonistic action of specific ligands. The difference and main advantage of these recombinant assays compared with conventional assays (brain membrane preparations, cell lines) is the purity of the receptor/channel preparation because only the recombinantly expressed neuronal calcium channel subtype is present in a suitable number on an animal cell surface. This is an essential precondition for the selection of specific neuronal ligands which ought if possible to have no effect on calcium channels of non-neuronal tissue types.

Some examples of the use of the recombinant screening assays described above are listed hereinafter.

1. Receptor binding assay

The animal cells transformed with human calcium channels (example: see above) can be cultivated and employed for the preparation of membranes. These membrane preparations can be employed in binding studies with various classes of radioactively labelled substances (Examples 1–5) for screening novel ligands (competitive assay). Examples of known calcium channel binding substances are:

1. Phenylalkylamines,
2. Benzothiazepines,
3. Dihydropyridines,
4. Bisphenylbutylpiperidines,
5. Omega conotoxins.

2. Calcium-45 flux assay

The cell membranes of cultured cells which have been transformed with human calcium channel subtypes can be depolarised with potassium ions or with alkaloids such as, for example, Veratridine. Membrane depolarisation leads to opening of calcium channels, which results in an influx (flux) of calcium ions into the cells. This voltage-dependent calcium influx can be measured using radioactively labelled calcium ($^{45}Ca$) (Example: Messing et al., 1985, J. Pharmacology and Exp. Therapeutics 235: 407–411) and employed for the functional testing/screening of calcium channel antagonists or agonists.

3. Fura 2 assay

Human calcium channel expressing animal cells (see above) can be employed in the presence of calcium-sensitive, fluorescent dyes (for example fura 2 or fluoro 3) for measurements of the intracellular calcium concentration after opening and blocking of the calcium channels (Example: Rosario et al., 1989, Neurosci. 29, 735–747). The change in the intracellular calcium concentration can in this case be measured by fluorimetry (spectrophotometry). This recombinant cell system can be employed as functional assay for finding subtype-specific calcium channel ligands (agonists and antagonists).

4. Electrophysiology

The calcium currents generated by membrane depolarisation can be measured electrophysiologically (Example; Carbone et al., 1990, Pflügers Arch., 416: 170–179). The effect of potential calcium channel antagonists or agonists can be physically measured and pharmacologically characterised directly on human calcium channels using the recombinant animal cell lines (see above).

5. Indirect methods of measurement

Many cellular processes are controlled by the intracellular calcium ion concentration (for example receptor-mediated signal transmission, various enzyme reactions, such as, for example, phosphorylation, dephosphorylations, neurotransmitter release, Ca-dependent gene regulation etc). Some of these biochemical reactions can be measured using a specific assay. It is thus possible in a recombinant calcium channel-expressing cell system to detect indirectly (physiologically) the effect of calcium channel modulators on calcium-dependent cellular processes (Exhale: Zernig et al., 1986, Eur. J. Pharmacol. 128., 221–229).

It is additionally possible by modifications introduced by targeted mutageneses, such as, for example, point mutations, insertions, deletions, replacement of DNA segments of various calcium channel subtypes, to detect direct effects on physiological processes (Example: Yool and Schwarz, 1991, Nature 349: 700–704).

Cloning strategy

1. Screening of the cDNA library 1.1. Plating of the cDNA library and processing of the nitrocellulose filters The plating of the cDNA library (human hippocampus in Lambda ZAPII, supplied by Strategene Inc., La Jolla, Calif., USA; Cat. No. 936205) and of the nitrocellulose filters was carried out as stated by the manufacturers or described by Sambrook et al., 1989, Molecular Cloning, A laboratory manual, Cold Spring Harbor Laboratory Press, New York, N.Y., USA.

1.2 Hybridisation probes

The primary hybridisation probe used was a synthetic antisense oligonucleotide which is complementary to a 40 bases-long fragment (pos. 361–400) of the DNA sequence of the beta subunit from rabbit skeletal muscle:

5'-CTTAAGGCTTCCCGGTCCTCCTCCAGG-
GAGACATCAGAGT-3'

The said DNA sequence can be obtained from the EMBL data bank under Access No. M25817.

The 1.9 kB-long cDNA fragment HB26 was isolated from the abovementioned cDNA library with the aid of this oligonucleotide. This fragment was employed as hybridisation probe in all subsequent screening experiments.

1.3 Labelling of hybridisation probes with radioactive DNA precursors

Oligonucleotides were enzymatically labelled with $^{32}$P-dCTP ("DNA Tailing Kit", Boehringer Mannheim GmbH, Postfach 310120, D-6800 Mannheim; Cat. No. 1028707).

cDNA fragments are labelled with $^{32}$P-dCTP using the "Random Primed Labeling Kits" (Boehringer Mannheim GmbH, Cat. No. 10004760).

1.4 Hybridisation and washing conditions 1.4.1. Oligonucleotides

The nitrocellulose filters were hybridised with the radioactively labelled hybridisation probe in the following solution at 42° C. overnight:

5× Denhardt's solution

5× SSC

50 µg/ml herring sperm DNA 50 mmol/l Na phosphate 1 mmol/l Na pyrophosphate

60 µg/ml ATP

The filters were washed with 2×SSC, 0.1% SDS at 55° C.

1.4.2. cDNA fragments

The nitrocellulose filters are hybridised with a radioactively labelled probe in the solution mentioned in 1.4.1., which was, however, made up with 50% formamide, at 42° C. overnight.

The filters were washed with 0.2×SSC, 0.1% SDS at 55° C.

Then Kodak X-Omat AR X-ray film was exposed with intensifying screens to the filters at −80° C. for various times.

2. Isolation of the lambda phages, subcloning and sequencing of the cDNA inserts 2.1 Conversion of the cDNA inserts into plasmids The cDNA inserts from positive Lambda ZAPII phages were removed and converted into the plasmid form according to a protocol of the manufacturer (Stratagene) using an fl-derived helper phage.

2.2. Determination of size and analysis of sequence of the cDNA inserts

Plasmid DNA was prepared from XL1-blue cells which harboured a recombinant pBluescript plasmid (Sambrook, J., et al., (1989) in: Molecular cloning, A laboratory manual, Cold Spring Harbor Laboratory Press, New York, N.Y.) and 0.5 µg samples of this DNA were treated with the restriction enzyme EcoRI. It was possible to deduce the total length of the inserted cDNA from the number and size of the resulting DNA fragments. The nucleotide sequence of the cDNA present was determined with SEQUENASE (USB, Cleveland, Ohio, USA) by the Sanger method on double-stranded DNA.

3. Description of the cDNA clones isolated to date for human neuronal beta subunits 3.1. HB26: length 1.9 kB This cDNA clone was isolated using the oligonucleotide described under 1.2. It contains a large portion of the coding region and an intron of about 450 base pairs.

HB26 was employed as cDNA probe for the isolation of other specific cDNAs from the human hippocampal Lambda ZAPII library:

3.2. HBB1: length 1.6 kB

This clone contains the complete coding region of a human neuronal beta subunit with 92% homology to the beta subunit from rabbit muscle. HBB1 is the sequenced portion of HB26-3 which is a total of 1.9 kB long.

3.3. HBB2: length 1.8 kB

This clone represents another subtype of human neuronal beta subunits with 74% homology to the beta subunit from rabbit muscle. HB28t7 is a partial sequence of the complete HBB2 clone. HB28t7 has a sequence that corresponds to bases 124–1299 of sequence HBB2. Since HB28t7 contains several reading errors which were corrected in sequence HBB2, there is no perfect identity of sequence HB28t7 and bases 124–1299 of sequence HBB2.

3.4. HBB3: length 1.8 kB

This clone represents a third subtype of human neuronal beta subunits. Up to position 1288, the cDNA shows 92% homology to the beta subunit from rabbit muscle. From position 1289 on, no homology to the rabbit muscle type is detectable.

All four listed clones show by comparison with the beta subunit of rabbit muscle a deletion of 45 amino acids which is characteristic of neuronal beta subunits.

The HBB1 sequence listing comprises 1612 bp and contains the complete coding region.

The HBB2 sequence listing comprises 1830 bp and contains the complete coding region.

The HBB3 sequence listing comprises 1805 bp and likewise contains the complete coding region.

---

We claim:

1. Isolated or synthetic DNA having a sequence consisting of SEQ ID NO: 2.

2. Isolated or synthetic protein encoded by the isolated or synthetic DNA according to claim 1.

3. A process of producing a human Ca++ channel β subunit, comprising expressing isolated or synthetic DNA according to claim 1 in a eucaryotic cell selected from the group consisting of Xenopus oocytes, insect cells and mammalian cells.

4. Isolated or synthetic DNA having a sequence consisting of SEQ ID NO: 3.

5. Isolated or synthetic protein encoded by the isolated or synthetic DNA according to claim 4.

6. A process of producing a human Ca++ channel β subunit, comprising expressing isolated or synthetic DNA according to claim 4 in a eucaryotic cell selected from the group consisting of Xenopus oocytes, insect cells and mammalian cells.

7. A process of producing a recombinant cell expression system, comprising coexpressing:

(a) isolated or synthetic DNA having a sequence consisting of SEQ ID NO: 1;

(b) isolated or synthetic DNA having a sequence consisting of SEQ ID NO: 2;

(c) isolated or synthetic DNA having a sequence consisting of SEQ ID NO: 3; and (d) the alpha-1 and alpha-2 subunit of mammalian voltage-operated calcium channels;

in a eucaryotic cell selected from the group consisting of Xenopus oocytes, insect cells and mammalian cells.

8. The recombinant cell expression system produced according to the process of claim 7.

9. A method of screening for substances that modulate the activity of voltage-operated calcium channels, said method comprising the following steps:

(a) incubating the recombinant cell expression system according to claim 8 with a substance suspected of being capable of modulating the activity of voltage-operated calcium channels; and (b) determining agonistic or antagonistic binding of said substance to voltage-operated calcium channels contained in said recombinant cell expression system; wherein agonistic or antagonistic binding indicates the capacity of said substance to modulate the activity of voltage-operated calcium channels.

* * * * *